United States Patent [19]

Schenck

[11] 4,238,757
[45] Dec. 9, 1980

[54] FIELD EFFECT TRANSISTOR FOR DETECTION OF BIOLOGICAL REACTIONS

[75] Inventor: John F. Schenck, Schenectady, N.Y.

[73] Assignee: General Electric Company, Schenectady, N.Y.

[21] Appl. No.: 668,584

[22] Filed: Mar. 19, 1976

[51] Int. Cl.³ .................. H01L 29/78; G01N 31/00
[52] U.S. Cl. ................... 357/25; 23/230 B;
       73/23; 73/61 R; 357/23; 357/41
[58] Field of Search ................ 357/23, 25, 26;
       23/230 B, 254 R; 73/23, 61 R, 61.1 R, 61.2

[56] References Cited

U.S. PATENT DOCUMENTS

| 3,831,432 | 8/1974 | Cox | 357/25 |
| 3,853,467 | 12/1974 | Giaever | 23/230 B |

OTHER PUBLICATIONS

Matsuo et al., IEEE Trans. Bio-Med. Engrg., vol. BME 21, Nov. 1974, pp. 485-487.
Esashi et al., Suppl. Journ. Japan. Soc. Appl. Phys., 1975, pp. 339-343.
Moss et al., Analytical Chemistry, vol. 47, pp. 2238-2243, (Nov. 1975).
Bergveld, IEEE Trans. Bio-Med. Engrg., vol. BME 19, Sep. 1973, pp. 342-351.

Primary Examiner—William D. Larkins
Attorney, Agent, or Firm—Marvin Snyder; James C. Davis

[57] ABSTRACT

A field effect transistor including conventional source and drain electrodes employs, in the gate region, a layer of antibody specific to a particular antigen. An electrolyte solution such as 0.155 Normal sodium chloride atop the antibody layer provides a predetermined drain current versus drain voltage characteristic for the device. Replacement of the electrolyte solution with another electrolyte solution containing the antigen alters the charge of the protein surface layer due to the antigen-antibody reaction, thus affecting charge concentration in a semiconductor inversion layer in the transistor. The time rate of change of drain current thus provides a measure of the antigenic protein concentration in the replacement solution.

17 Claims, 3 Drawing Figures

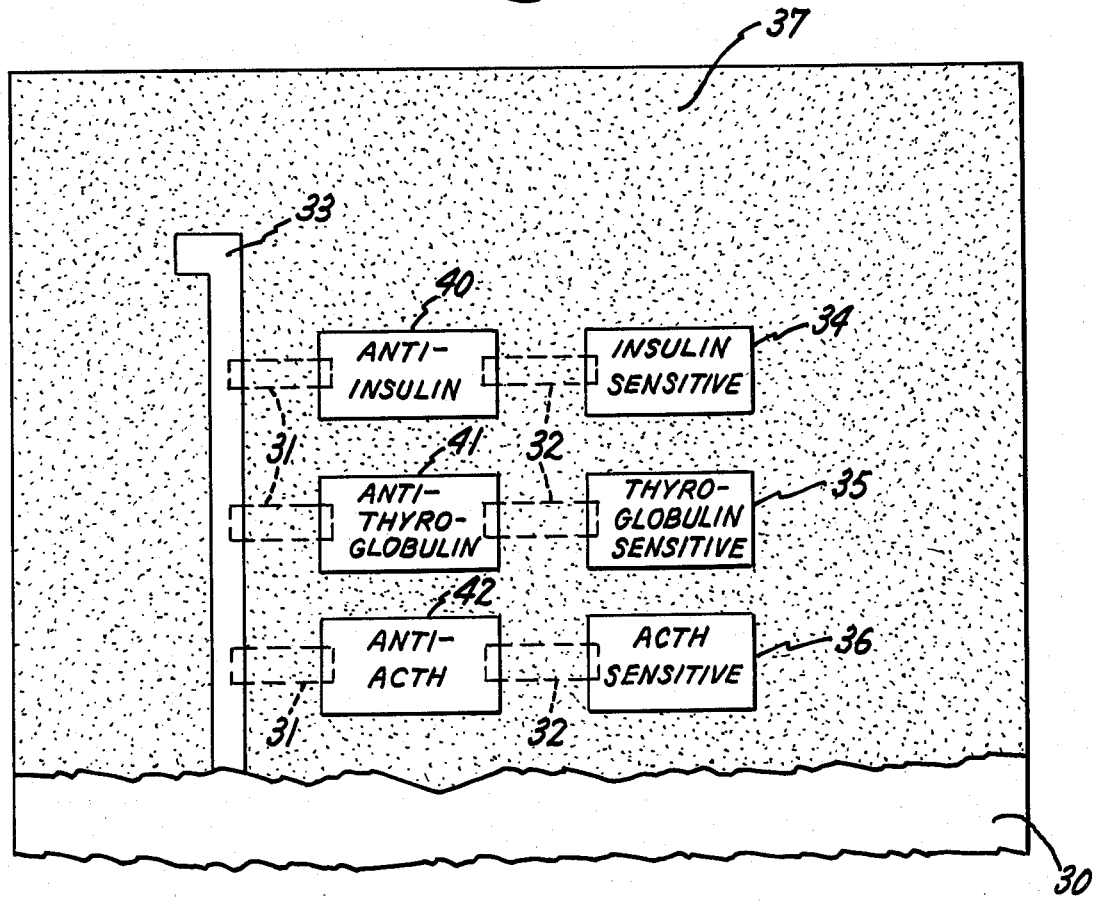

FIELD EFFECT TRANSISTOR FOR DETECTION OF BIOLOGICAL REACTIONS

INTRODUCTION

This invention relates to sensing of biological reactions, and more particularly to a method and apparatus for employing a field effect transistor device to detect specific biological reactions and parameters associated therewith.

In I. Giaever U.S. Pat. No. 3,853,467, issued Dec. 10, 1974 and assigned to the instant assignee, it is noted that a given protein will adhere to a substrate in a monomolecular layer only and that no arbitrary protein layer will adhere to the given protein layer, but that a protein which specifically reacts with the given protein will immunologically bond thereto. The present invention is concerned with an electronic technique for detecting such reaction.

The human body contains a large number of different types of protein molecules. They include structural elements such as collagen and elastin, contractile materials such as actin and myosin, antibody proteins used to protect against infectious disease, and transport molecules such as hemoglobin, albumin and ceruloplasmin. There are also many proteins which have been identified but whose function within the body is not yet known. Moreover, many of the hormones such as insulin, growth hormone estrogen, and gastrin are either proteins or closely related molecules. The concentrations of these various materials are crucial guides to the state of health or disease of the patient. However, it is presently very difficult and expensive to determine concentration of most of these materials accurately, and it is not normally done unless a compelling reason exists. Moreover, though immunological methods of assaying various proteins have recently been developed, they are, nevertheless, time-consuming and expensive and must be performed by a trained technician with good judgment. It is therefore desirable to develop simple techniques to allow determination of a large number of proteins at a more rapid rate, with less cost, and less dependence on technician judgment, than have heretofore existed.

Recently, a large body of knowledge has been developed on device-related properties of semiconductor surface physics. A dramatic practical application has been in field effect transistors for large-scale integration. However, other significant applications have been made in charge coupled devices, and in surface stability and reliability of all semiconductor devices. Very limited application of this work, however, has been made in the area of devices for monitoring biological processes. Additionally, while there has also been great interest in developing immunological assay techniques for detection and quantification of proteins, there has been a dearth of applications of semiconductor devices to accomplish the necessary sensing.

A device usable for accomplishing the sensing necessary in developing immunological assay techniques of the aforementioned type is the field effect transistor, or FET. Such device may typically comprise a channel of semiconductor material with an ohmic connection at each of its two opposite ends, termed the source and drain, respectively. The source comprises the contact which supplies a current of majority carriers to the channel, while the drain comprises the contact where a current of majority carriers leaves the channel. Voltage applied to a gate electrode controls current magnitude between the source and drain electrodes in either the enhancement mode, whereby the gate is operated at a voltage of appropriate amplitude to induce free carriers into the channel, or the depletion mode, whereby the gate is operated at a voltage of amplitude necessary to reduce channel conductance to a desired operating level. In FETs of the insulated gate type, the gate electrode, typically of metal, is located atop an insulating layer, such as an oxide coating, situated above the channel.

P. F. Cox U.S. Pat. No. 3,831,432, issued Aug. 27, 1974, is directed to a sensor comprised of a type of field effect device which employs source and drain electrodes at each end of a channel of semiconductor material. Instead of a gate electrode, however, a chemically specific film is formed in the gate region directly atop, and in contact with, the channel. Adsorption in the gate film of specific contaminants which are polar results in establishment of a localized field, causing the bulk semiconductor material to accumulate charges near the surface to offset the field. The accumulated charges dominate the bulk electrical properties near the surface, thus modulating flow of free carriers through the channel. Hence the gate region is left floating; that is, no predetermined potential is applied to the gate.

The present invention is directed to a field effect device in which material acting as a gate electrode is applied atop a thin insulating oxide layer situated above the channel of semiconductor material. By controlling the gate voltage, a quiescent operating point may be selected for maximum sensitivity to gate voltage. Hence by varying gate voltage in accordance with any sensed parameter, a change in drain current constitutes a measure of the sensed parameter. Additionally, since the gate electrode may typically be comprised of a liquid, a thinner gate oxide layer than used in conventional FETs may be employed. This is because metal-to-semiconductor short circuits which can occur through microscopic voids extending through the entire thickness of the oxide film are not possible when the gate voltage is applied to a nonmetallic electrolytic conductor. As a result, the device can exhibit a higher transconductance than conventional FETs. Moreover, the material of the gate electrode is readily removable, facilitating reusability of the device.

Accordingly, one object of the invention is to provide a field effect device capable of sensing presence of particular biological substances.

Another object of the invention is to provide an insulated gate field effect transistor, capable of functioning in either the enhancement or depletion mode, as a reusable sensor of particular biologicalsubstances.

Another object is to provide a fast, inexpensive technique for quantitatively determining concentration of a wide variety of proteins in solution.

Another object is to provide a field effect transistor employing a liquid gate electrode.

Another object is to provide an FET of very high transconductance.

Briefly, in accordance with a preferred embodiment of the invention, a field effect transistor comprises a substrate of semiconductor material of one conductivity type, and first and second separated regions of opposite conductivity type in the substrate extending a predetermined distance into the substrate from the upper surface thereof. Each of the first and second regions, respectively, are situated at, and define, opposite ends of a channel region of the one conductivity type semiconductor material. First and second electrical conducting means contact each of the first and second separated regions of opposite conductivity type, respectively, and an insulating coating overlays the substrate of semiconductor material atop the channel region. A monomolecular layer of a first protein is adsorbed atop the insulating coating. A fluid specimen suspected of containing a second protein that specifically reacts with the first protein is applied atop the layer of the first protein, and contact to the fluid specimen is made by third electrical conducting means.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings in which:

FIG. 3 is a plan view of an integrated circuit employing the instant invention.

DESCRIPTION OF TYPICAL EMBODIMENTS

Figure 1:
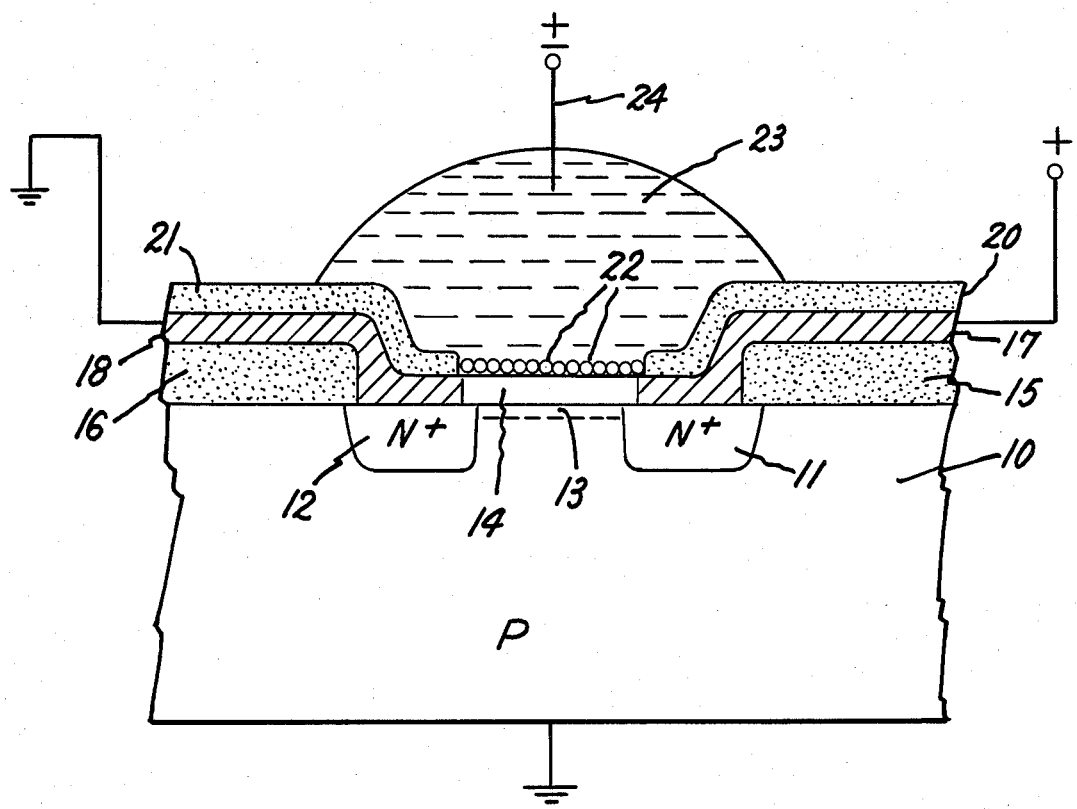
FIG. 1 is a cross sectional view of apparatus embodying the instant invention.

FIG. 1 illustrates the FET of the invention as comprising a monocrystalline substrate of semiconductor material of one conductivity type, such as P-type silicon 10, with relatively heavily-doped source and drain regions 11 and 12, respectively, of opposite conductivity type, indicated by N+ designations, extending for a predetermined distance into substrate 10 from the upper surface thereof. Regions 11 and 12 are typically formed by conventional diffusion of impurities into silicon 10. The length of an inversion layer or channel 13 formed in the upper portion of substrate 10 is demarcated by regions 11 and 12 which are situated at opposite ends thereof. A suitable insulating layer 14, such as of silicon dioxide or silicon nitride, is produced in conventional fashion. For example, silicon dioxide may be produced, such as by thermal growth in an oxidizing atmosphere, atop substrate 12 so as to cover inversion layer 13 completely with a uniform thickness of insulating material. Additional insulating layers 15 and 16, such as of thermally-grown silicon dioxide or silicon nitride, are situated atop substrate 12 outside the locations where metallic regions 17 and 18 make ohmic contact to source and drain regions 11 and 12, respectively, in conventional fashion. Metallic regions 17 and 18, such as of aluminum, are produced in conventional fashion atop layers 15 and 16, respectively, as by evaporation thereon. The thickness of insulating layer 14 may be in the range of about 20 angstroms to at least 1,000 angstroms, and is typically about 300 angstroms, while insulating layers 15 and 16 may be about 5,000 angstroms thick.

Insulating layers 20 and 21 are coated atop metallic regions 17 and 18, respectively, and may be comprised of silicon dioxide or silicon nitride deposited thereon. These layers protect against short-circuits between the gate and either of the source and drain regions by precluding any gate material from contacting either of metallic regions 17 and 18.

Figure 2:
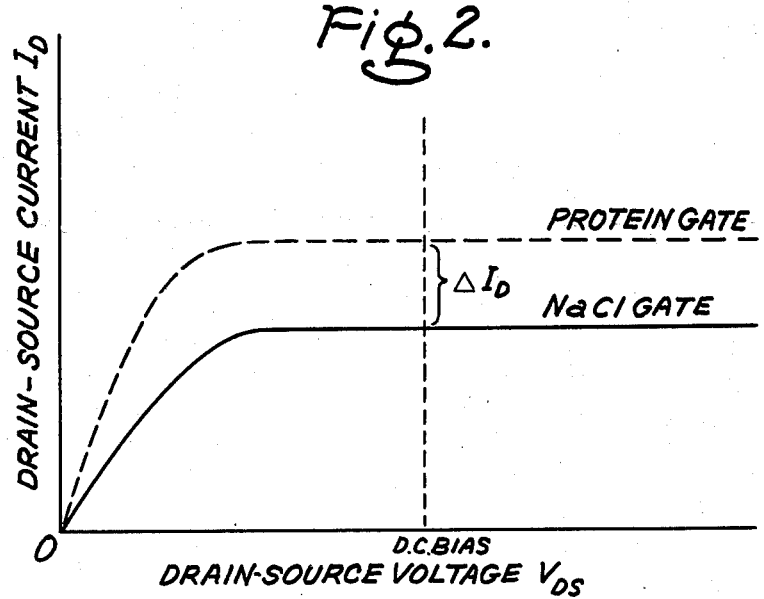
FIG. 2 is a plot of operating characteristics for apparatus of the type shown in FIG. 1.

Instead of a conventional metallic gate electrode, a monomolecular layer of a protein, such as antibodies 22 specific to an antigenic protein to be detected, is adsorbed atop thin insulating layer 14 by immersing the transistor in a solution of such protein, as described and claimed in the aforementioned Giaever Pat. No. 3,853,467. As a specific example, if the antigen sought is the polypeptide hormone human serum albumin, antibodies thereto are adsorbed on insulating layer 14 and the transistor may be operated in the depletion mode. An electrolyte solution of, for example, 0.155 Normal sodium chloride 23 is applied over the top surface of the transistor in the gate region, so as to be supported, at least partially, by antibodies 22. The solution is contacted by an electrode 24. Drain 11 is biased positive with respect to source 12 while voltage applied to sodium chloride solution 23 may be adjusted slightly negative or positive as required for optimum response. For a predetermined constant gate voltage, the drain-to-source current versus voltage characteristic follows the solid curve of FIG. 2.

It is well known that semiconductor surfaces, such as those of the FET gate region, are very sensitive to presence of electric charges in their vicinity, and that protein molecules such as human serum albumin and antibodies thereto are charged molecules. Thus, when sodium chloride solution 23 is replaced with a solution containing human serum albumin (i.e., with human serum) the charge on gate oxide 14, which corresponds to the charge of the adsorbed antibodies thereon, is altered by the reaction between the antigen and antibody, thus affecting the charge concentration in inversion layer 13 and hence the drain-to-source current. The drain-to-source current versus voltage characteristic then follows the dotted curve shown in the graph of FIG. 2. The time rate of this current change at any given drain-to-source voltage bias level constitutes a measure of the protein human serum albumin concentration in the serum.

Sensitivity of the device shown in FIG. 1 is variable over wide limits by appropriate choice of device geometry, with length, width, thickness and dielectric constant of gate insulation 14 being the most readily varied parameters. Thus sensitivity of the device, as represented by its transconductance, may be expressed as $$g_m = \frac{dI_D}{dV_G}$$

where $I_D$ is drain current and $V_G$ is gate voltage. However, drain current, in saturation, may be expressed as $$I_D = K(V_G - V_T)^2$$

where $V_T$ is the threshold voltage or gate voltage necessary to terminate conduction in a depletion mode device or initiate conduction in an enhancement mode. Thus $$g_m = 2K(V_G - V_T)$$

and $$K = \frac{\mu \epsilon_{ox} \epsilon_o W}{2 t_{ox} L}$$

where $\mu$ represents carrier mobility, $\epsilon_{ox}$ is the dielectric constant of the gate insulation, $\epsilon_o$ is the permittivity of free space, W is the width of the gate region in the substrate, $t_{ox}$ is the thickness of the gate insulation, and $L$ is the length of the gate region in the substrate.

The antibody or protein layer on gate insulation 14 leads to a change in threshold voltage by altering the surface charge density $Q_{ss}$ of the transistor and, since $$V_T = \Phi_{ms} - \frac{Q_{ss}}{C_o} + 2\phi_f - \frac{Q_B}{C_o}$$

where $\Phi_{ms}$ is the work function between the gate electrode and silicon, $\phi_f$ is the Fermi potential, $Q_B$ is the charge induced in the surface depletion layer generated by ionized donor atoms, and $C_o$ is the gate capacitance per unit area, the change in threshold voltage may be written $$\Delta V_T = \frac{\Delta Q_{ss}}{C_o}.$$

Also, $$\Delta I_D = g_m \Delta V_T$$

and therefore $$\Delta I_D = g_m \frac{\Delta Q_{ss}}{C_o}.$$

Those skilled in the art will appreciate that the foregoing analysis is simplified and assumes that the additional charge due to the protein or antibody layer on gate insulation 14 is mirrored entirely in the inversion layer of the device. In fact, much of the protein charge on antibody layer 22 is neutralized by small ions ($Na^+$ and $Cl^-$) in the serum and therefore sensitivity of the device may be enhanced if the serum is replaced with a less concentrated electrolyte solution once the antigen-antibody reaction has occurred at the gate oxide surface. The device thus described produces a time-dependent drain current having a rate of change proportional to the amount of antigenic protein in the serum sample.

The specificity of the antigen-antibody reaction makes it possible to develop an "immunological integrated circuit" as illustrated in FIG. 3. This device, shown partially cutaway, is constructed of a semiconductor material, such as silicon 30, having source diffused regions 31 and drain diffused regions 32. The source diffused regions are all interconnected by a metallic source contact 33 atop silicon wafer 30. Each of respective drain diffused regions 32 is connected to a separate metallic drain contact 34, 35 and 36, respectively. Each of the respective gate regions is coated with a separate antibody such that gate region 40 is coated with antiinsulin, gate region 41 is coated with antithyroglobulin and gate region 42 is coated with anti-ACTH. The remaining portion of the wafer is coated with an insulative coating, such as silicon dioxide 37. Except for the antibody coating on each of gate regions 40, 41 and 42, fabrication of the device of FIG. 3 is performed by conventional semiconductor integrated circuit fabrication techniques and deposition of the antibodies on each of gate regions 40, 41 and 42 is performed individually.

When the structure of FIG. 3 is immersed in human serum so that the antibodies on gate regions 40, 41 and 42 contact the serum in common, and electrical contact is made to each of the source and drain contacts and a common gate voltage is applied to the serum, current through each of drain contacts 34, 35 and 36 reflects the concentration of a specific, respective antigenic protein in the serum; that is, current through drain contact 34 constitutes a measure of insulin in the serum, current through drain contact 35 constitutes a measure of thyroglobulin in the serum and current through drain contact 36 constitutes a measure of ACTH in the serum. This structure, therefore, provides a separate measure for each of the antigens tested for, reflecting the concentration of each of the specific antigens in the serum. Each drain contact supplies an electronic signal proportional to a specific antigenic protein concentration, respectively, and each of these signals is readily available for further electronic processing so that measurement of such signals does not have to be performed by a specially trained technician. Those skilled in the art will note that the increase in thickness of the dielectric layer atop each gate, which results from deposition of the antigenic protein layers, may also be utilized to provide an electronic signal of useful proportions which is dependent upon the antibody-antigen reaction.

The invention may be employed in those instances where an entirely satisfactory technique for assaying particular proteins has not been known to exist. This includes detection of antibodies and antigens associated with infectious diseases and the levels of hormone concentration associated with endocrine disorders. The invention may also have particular utility where assessment of a large number of different proteins from a large number of patients (such as in mass screening programs) is necessary.

The foregoing describes a field effect device capable of sensing presence of particular biological substances, and a fast, inexpensive technique for quantitatively determining concentration of a wide variety of proteins in solution. The device constitutes an insulated gate field effect transistor capable of functioning in either the enhancement or depletion mode as a reusable sensor of particular biological substances. The field effect transistor exhibits very high transconductance while employing a liquid gate electrode. The device readily lends itself to replication in integrated circuit configuration.

While only certain preferred features of the invention have been shown by way of illustration, many modifications and changes will occur to those skilled in the art. For example, the protein molecules above the channel region in the semiconductor material of the device described herein could comprise antigens rather than antibodies, in which case the device would be useful in measuring antibody concentration in serum solutions. It is, therefore, to be understood that the appended claims are intended to cover all such modifications and changes as fall within the true spirit of the invention.

I claim:

1. A field effect transistor comprising:
   a substrate of semiconductor material of one conductivity type, said semiconductor material containing first and second separated regions of opposite conductivity type extending a predetermined distance into said substrate from the upper surface thereof, each of said first and second regions, respectively, being situated at, and defining, opposite ends of a channel region of said one conductivity type semiconductor material;

first and second electrical conducting means contacting each of said first and second separated regions of opposite conductivity type, respectively;

an insulating coating overlaying said substrate atop said channel region;

a monomolecular layer of a first protein adsorbed atop said insulating coating, said layer of said first protein being adapted to support a fluid specimen to be investigated; and third electrical conducting means adapted to make contact to said fluid specimen.

2. The apparatus of claim 1 wherein said monomolecular layer of a first protein comprises antibodies.

3. The apparatus of claim 2 wherein said fluid specimen comprises a solution to be tested for presence of antigens specific to said antibodies.

4. The apparatus of claim 1 wherein said semiconductor material comprises silicon and said insulating coating comprises silicon dioxide.

5. The apparatus of claim 1 wherein said semiconductor material comprises silicon and said insulating coating comprises silicon nitride.

6. The apparatus of claim 3 wherein said semiconductor material comprises silicon and said insulated coating comprises silicon dioxide.

7. The apparatus of claim 3 wherein said semiconductor material comprises silicon and said insulating coating comprises silicon nitride.

8. The apparatus of claim 1 wherein said fluid specimen comprises a solution containing an antibody concentration to be measured and said monomolecular layer of a first protein comprises antigen specific to said antibody.

9. The apparatus of claim 8 wherein said semiconductor material comprises silicon and said insulated coating comprises silicon dioxide.

10. The apparatus of claim 8 wherein said semiconductor material comprises silicon and said insulated coating comprises silicon nitride.

11. An integrated circuit comprising:

a wafer of semiconductor material of one conductivity type, said material containing a plurality of pairs of separated regions of opposite conductivity type in said wafer extending a predetermined distance into said wafer from the upper surface thereof, each pair of said regions defining opposite ends of a channel region therebetween of said one conductivity type semiconductor material;

a plurality of pairs of electrical conducting means contacting each of said pairs of separated regions of opposite conductivity type, respectively;

a conductive strip interconnecting one electrical conducting means in each of said pairs thereof;

an insulating coating overlaying said wafer atop each of said channel regions;

a monomolecular layer of different protein material adsorbed atop the insulating coating above each of said channel regions, respectively, each said layer of different protein material being adapted to contact, in common, a fluid specimen to be investigated; and third electrical conducting means adapted to make contact to said fluid specimen.

12. The apparatus of claim 11 wherein each said monomolecular layer of different protein material comprises a different antibody layer, respectively.

13. The apparatus of claim 12 wherein said fluid specimen comprises a solution to be tested for presence of antigens specific to any of the antibody layers adsorbed atop the insulating coating above each of said channel regions, respectively.

14. The apparatus of claim 12 wherein said semiconductor material comprises silicon and said insulating coating comprises silicon dioxide.

15. The apparatus of claim 12 wherein said semiconductor material comprises silicon and said insulating coating comprises silicon nitride.

16. The apparatus of claim 13 wherein said semiconductor material comprises silicon and said insulating coating comprises silicon dioxide.

17. The apparatus of claim 13 wherein said semiconductor material comprises silicon and said insulating coating comprises silicon nitride.

* * * * *